United States Patent
Di (12) United States Patent (10) Patent No.: US 6,493,418 B1
Di (45) Date of Patent: Dec. 10, 2002

(54) METHOD FOR PRECISELY MEASURING THE WEIGHT OF MASS MATERIAL AND NUCLEONIC WEIGHER EMPLOYING THIS METHOD

(76) Inventor: Shengcai Di, Rm.402/5,2F., Zhongli Baiwanzhuang Dajie, Beijing 100037 (CN)

( * ) Notice: Subject to any disclaimer, the term of this patent is extended or adjusted under 35 U.S.C. 154(b) by 335 days.

(21) Appl. No.: 10/049,416

(22) Filed: Feb. 8, 2002

(30) Foreign Application Priority Data

Aug. 10, 1999 (CN) ......................................... 99111339 A (51) Int. Cl.⁷ ............................................. G01N 23/06
(52) U.S. Cl. ........................................................ 378/54
(58) Field of Search ..................... 378/54–56

(56) References Cited

U.S. PATENT DOCUMENTS 3,489,901 A * 1/1970 Brown .......................... 378/54
3,541,332 A * 11/1970 Brunton ........................ 378/54
5,585,603 A * 12/1996 Vogeley ........................ 378/54

* cited by examiner

Primary Examiner—Craig E. Church
(74) Attorney, Agent, or Firm—McDonnell Boehnen Hulbert & Berghoff (57) ABSTRACT

The present invention discloses a method for precisely measuring the weight of mass material and a nucleonic weigher employing this method. It is characterized in that the coefficient K in the nucleonic weigher's weighing formula $F=KLn(U_i/U_0)$ is dynamically modified, based on the variations of the parameters including the flowrate, the position on the conveying device, and the piled shape of the weighed mass material and the scattering of gamma radiation, thus improving the measuring precision. The nucleonic weigher manufactured with a completely enclosed framework has the merits of high measuring precision, wide application, good stability, reliable safety, small maintenance, and low cost.

7 Claims, 6 Drawing Sheets

Fig.1

A → the small load    B → the large load

METHOD FOR PRECISELY MEASURING THE WEIGHT OF MASS MATERIAL AND NUCLEONIC WEIGHER EMPLOYING THIS METHOD

FIELD OF THE INVENTION

The invention refers to a method for measuring mass material's weight especially refers to the use of nuclear radiation high precision measuring of mass material's weight with high precision nucleonic weigher (nucleon scale) to apply this method.

BACKGROUND OF THE INVENTION

Nucleonic weigher (nucleon scale) is manufactured on the research basis of material's absorption principle to gamma ray.

Figure 1:
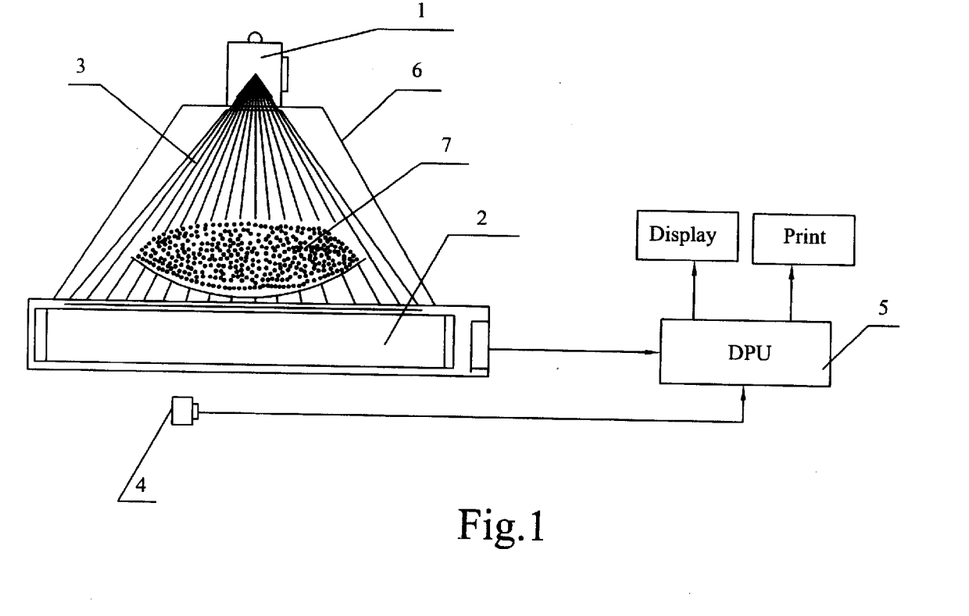
FIG. 1 is a diagram of nucleon scale applying existing technique.

The existing nucleon scale's operation principle is shown in FIG. 1. In this diagram, the nucleon scale includes a gamma radiation source (1), a gamma ray detector (2), a gamma ray radiation area (3), a speed measuring device (4), a Data Processing Unit (DPU) (5), a scale frame and protecting case (6), a conveyer belt and mass meterial (7). On the top of nucleon scale's frame there sets the gamma radiation source and underneath the frame there sets gamma ray detector. Conveyer belt with bulk mass material go through the frame. Gamma ray radiation source steadily emits gamma ray with constant intensity. When the belt carries no material the gamma ray received by the gamma ray detector is also a constant and at same time the gamma ray detector's output voltage is $U_0$ and when the belt carries material a part of gamma ray emitted by the radiation source is absorbed by mass material and the rest part penetrating mass material is received by the gamma ray detector and at same time the gamma ray detector's output voltage is $U_i$. According to material's absorption law to gamma ray it is known that $U_0$, $U_i$ and the mass material have the following relations:

$$U_i = U_0 e^{-\mu_\rho \rho d} \quad (1)$$

where $\mu_\rho$—material's mass absorption coefficient to gamma ray

ρ—material's density d—material's thickness to move line and also to multiply S/S on the exponent so we get $$\frac{U_i}{U_0} = e^{-\mu_\rho \rho d S/S} \quad (2)$$

$$W = \rho d s$$

$$\frac{U_i}{U_0} = e^{-\mu_\rho W/S}$$

where S—material's area on the belt to apply logarithm on both sides of formula (2) and let W/S=F, K=−1/$\mu_\rho$ so we get $$F = K \times \mathrm{Ln}\frac{U_i}{U_0} \quad (3)$$

where F—material's load;

K—material's rating coefficient;

The conveyer belt's speed V can be measured by the speed sensor so material flow P on the belt is: P=FV The accumulative mass material $W_h$ moved in a period of time is:

$$W_h = \sum_{i=1}^{n} F_i V_i \quad (4)$$

Figure 2:
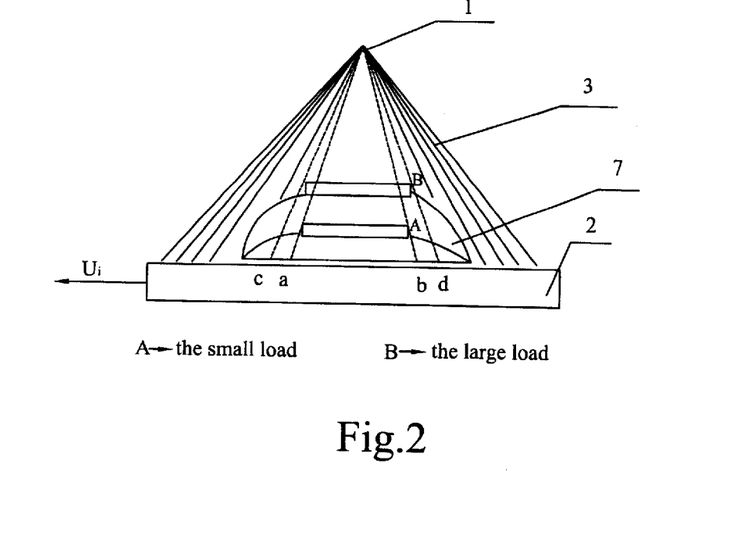
FIG. 2 is a diagram of mass material's absorption situation to gamma ray at different positions.

The existing scale takes K as a constant in formula (3) but actually K is not a constant and it varies with the change of belt load. The main cause is the existing nucleon scale makes 2 approximations while applying absorption law to gamma ray by material and they are:

1) to assume scattering factor=1 is to ignore the gamma ray scattering influence. In fact, the more density and thickness as mass material has, the bigger influence as scattering gets.
2) the absorption law of gamma ray by mass material requires gamma ray in parallel, but actually the existing nucleon scale is to use spot source which produces fan beamed gamma ray as shown in FIG. 2. When material is on position A the absorbed gamma ray situates on plane a-b and when material is on position B the absorbed gamma ray situates on plane c-d. Obviously c-d is greater than a-b.

Therefore, change of material load, piling shape with difference of positions plus the influence of scattering factor is the main cause to restrict measuring precision of the existing nucleon scale.

At present nucleon scales available at home and abroad all adopt mass material total weight to rate coefficient K, such as Chinese Patent ZL95106808.3 (Announced Patent No.CN1039160C). Using this method to rate coefficient K the nucleon scale records only material's weight but not the change of material's load so the rated coefficient K is of no relation with belt's material load and does not meet the actual situation. Evidently the existing nucleon scale can not proceed instantaneous correction to coefficient K according to belt load variation so it has rather big measuring error with less precision.

SUMMARY OF THE INVENTION

An aim of this invention is to solve the above mentioned problem. It provides a dynamic high precision measuring method to reduce and eliminate influence to measuring accuracy in respect of change of material load, piling shape with difference of positions plus the influence of scattering factor and also to proceed dynamic correction. The high precision nucleon scale is manufactured to apply this method. In order to realize above mentioned aim the invention adopts following technique schemes:

A method for measuring mass material's weight with high precision is to include following steps:

(1) installing multiple gamma radiation sources with corresponding gamma ray detectors and in between them to install the mass material conveyer device;

(2) measuring the gamma ray detector's output voltages $U_0$ with no material and $U_i$ with material to input to DPU which is connected to gamma ray detector;

(3) using the speed sensor to measure moving speed $V_i$ of the conveyer device to input to DPU (PLC or industrial control machine) which is connected to speed sensor;

(4) the DPU calculates the accumulative weight W transmitted in a period of time according to formula:

$$W = \sum_{i=1}^{n} KLn(U_i/U_0)V_i$$

The material rated coefficient K in the formula is dynamically corrected to follow the change of mass material's load and influence of gamma ray scattering. The above mentioned material rated coefficient K to follow the change of material load is determined by object's rated method with following steps:

(1) to use a standard scale to read out material's weight $W_{aB}$. The conveyer device steadily transmits mass material's load to nucleon scale for measurement;

(2) from instantaneously collected parameters of gamma ray detector's output voltage $U_i$, speed sensor's moving speed $V_i$, and transmission time $t_i$ to calculate formulae:

$$F_{Ba} = \frac{W_B}{\sum_{i=1}^{n} V_i t_i} \quad \left(Ln\frac{u_i}{u_0}\right)_{aAVG} = \frac{\sum_{i=1}^{n} Ln\frac{U_i}{U_0}}{n}$$

Figure 3:
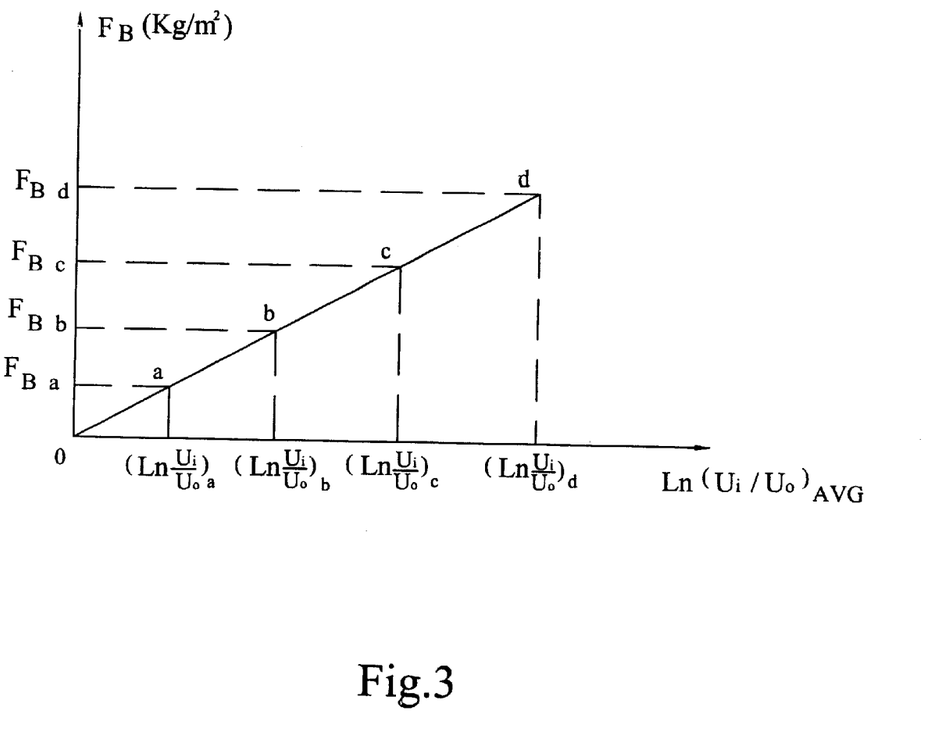
FIG. 3 is a diagram of functional relation curve of $F_B$ with $Ln(U_i/U_0)$.

Set up a coordinate system with $F_B$ as ordinate and $LnU_i/U_0$ as abscissa. According to the calculated $F_{Ba}$ and $(LnU_i/U_0)_{aAvG}$ to determine point a in the coordinate system to get K which is the sloping rate of 0a;

(3) Corresponding to different material weights $W_{bB}$, $W_{eB}$, $W_{dB}$ ... to adopt same method as above we can determine points b, c, d ... in the coordinate system. Hence we get Kb, Kc, Kd ... and functional relation of $F_B=f(LnU_i/U_0)$ as shown in FIG. 3.

Using multi-section's linear relation of $F=b_j+k_jLn(U_i/U_0)$ to replace function $F_B=f(LnU_i/U_0)$ where j is linear section numbers we have following steps:

(1) to connect 0a, ab, bc, cd ... to get each linear section;

(2) to utilize 0, a, b, c, d ... each point's coords value to separately get each linear section's b and k; or to use multi-items method to joint $F_B=f(LnU_i/U_0)$. For a, b, c, d ... each point coordinates to use minimum 2 multiplication method to get coefficients $a_0, a_1, a_2 ... a_K$ from multi-items formula: $F=a_0+a_1(LnU_i/U_0)+a_2(LnU_i/U_0)^2+ ... +a_k(LnU_i/U_0)^k$ where k=0, 1, 2, 3 ... k.

It is another object of this invention to provide a nucleon scale with high measuring precision, wide application, good stability, small maintenance and low cost.

A nucleon scale applying above mentioned method is to include:

1–N gamma radiation sources where N=2–10.

Gamma ray detector corresponds to gamma radiation source which transfers gamma ray intensity into voltage parameter. The mass material's conveyer device is installed between the detectors and radiation sources.

Speed sensor can measure moving speed of the mass material's conveyer device.

Micro-computer or DPU (PLC) connected to gamma ray detector and speed sensor can calculate mass material's accurate weight according to said method.

The forenamed gamma radiation sources can be selected from $^{137}CS$, $^6Co$, $^{241}Am$ according to the mass material to be measured. The number of sources is determined by width of mass material's conveyer device with optimum 2–7.

The forenamed gamma radiation sources and gamma ray detectors can be fixed on counter positions in a completely enclosed scale frame.

Figure 4:
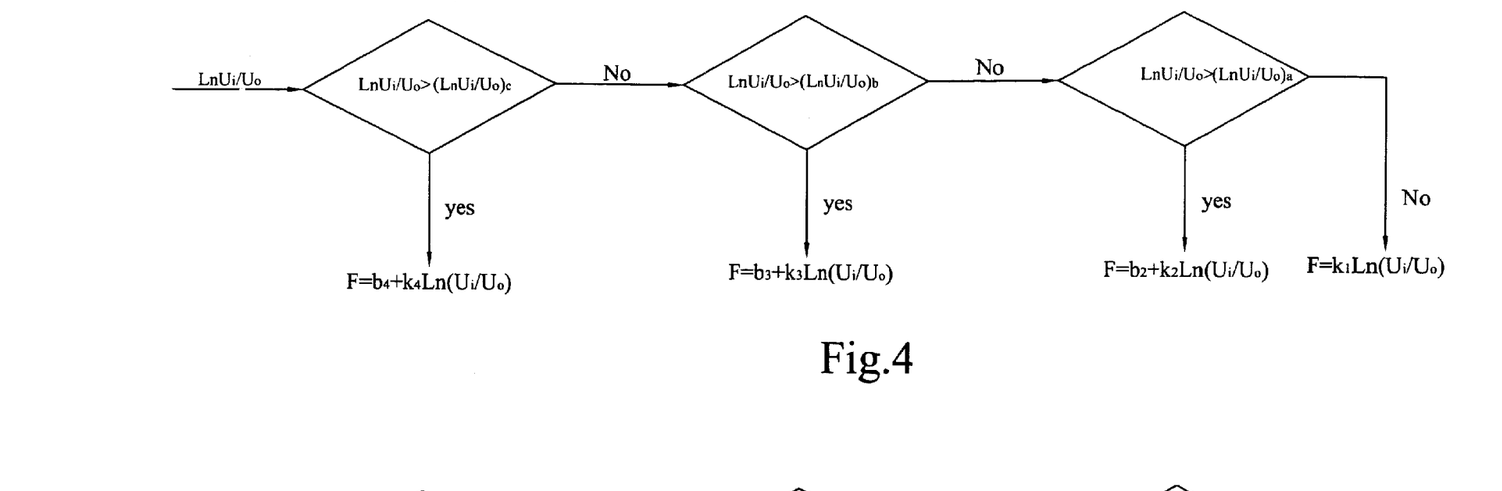
FIG. 4 is a diagram of flow prediction at broken line position.

When using multi-section's linear relation to joint function $F_B=f(LnU_i/U_0)$ the above mentioned nucleon scale is to operate according to broken line position's process prediction scheme as shown in FIG. 4.

This invention covers following advantages:

The dynamic high precision measuring method eliminates the influence to measuring accuracy from change of mass material's load, piling shape with difference of material positions plus the influence of gamma ray scattering factor therefore, it greatly improves measuring precision. The nucleon scale applying this method has high measuring precision to suit for wide range of material's flow with broad field of application covering good stability and wider range of application of radiation source therefore, it is either cost effective or highly accurate, safe and reliable.

DETAILED DESCRIPTION OF THE PREFERRED EMBODIMENT

Hereinafter is further explanation to this invention with attached Figures:

Adopting load method for the nucleon scale to give rate to mass material's rated coefficient K:

Assume at time of object rating DPU from nucleon scale measured $U_0=5v$, $U_i=4.5v$, belt speed V=1 m/s and transmission time t=180 sec, standard scale weighed material's weight $W_{aB}$=1800 kg and according to formulae:

$$F_{Ba} = \frac{W_B}{\sum_{i=1}^{n} V_i t_i} \left( Ln \frac{u_i}{u_0} \right)_{aAVG} = \frac{\sum_{i=1}^{n} Ln \frac{U_i}{U_0}}{n}$$

We can calculate $F_{Ba}$, $Ln(U_i/U_0)$, belt length and mass material's rated coefficient K. Set up coordinate system to take $F_{Ba}$ as ordinate and $Ln(U_i/U_0)$ as obscissa. Determine point a according to average value of $F_B$ and $Ln(U_i/U_0)_{aAVG}$ and thereafter orderly change material's load by using same method to determine points b,c, d . . . with data listed in Table 1:

TABLE 1

| Rated numbers | 1 | 2 | 3 | 4 |
|---|---|---|---|---|
| Coordinate point | A | B | C | D |
| Belt length L = V · t | 180 m | 150 m | 130 m | 110 m |
| $U_1$ | 4.5 v | 4 v | 3.5 v | 3 v |
| Average value of Ln $(U_i/U_0)_{Aavg}$ | −0.10536 | −0.22314 | −0.35667 | −0.51082 |
| Standard scale weighed material's weight $W_B$ | 1800 kg | 3150 kg | 4303 kg | 5172 kg |
| Mass material's load $F_B = W_B/L$ | 10 kg/m | 21 kg/m | 33.1 kg/m | 47 kg/m |
| Mass material's rated coefficient K | 94.96 | 94.11 | 92.80 | 92.00 |

Figure 5:
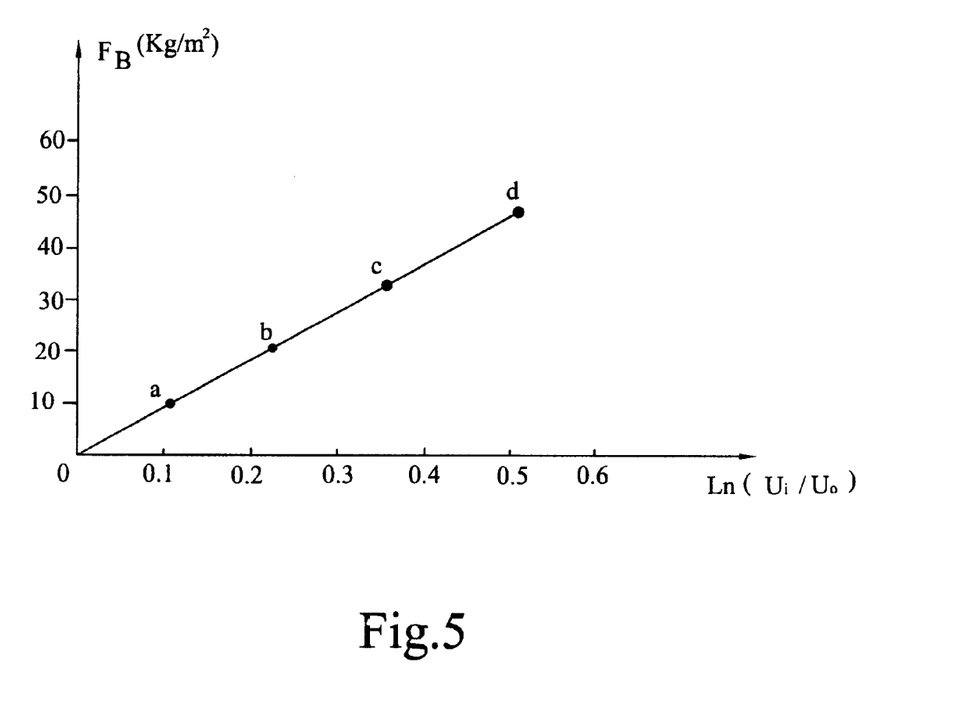
FIG. 5 is a diagram of functional relation curve of $F_B$ with $Ln(U_i/U_0)$ in implementation.

1) Joint with broken line method to connect 0a, ab, bc, cd each line and use two points make a line method to get each line's cut off distance and sloping rate as shown in Table 2, FIG. 5.

TABLE 2

| Line | 0a | ab | bc | Cd |
|---|---|---|---|---|
| Cut off distance $b_j = (y_1x_2 − y_2x_1)/(x_2 − x_1)$ | O | 0.1691 | 0.7790 | 0.9533 |
| Sloping rate $k_j = (y_2 − y_1)/(x_2 − x_1)$ | 94.96 | 93.37 | 90.63 | 90.14 |

Figure 6:
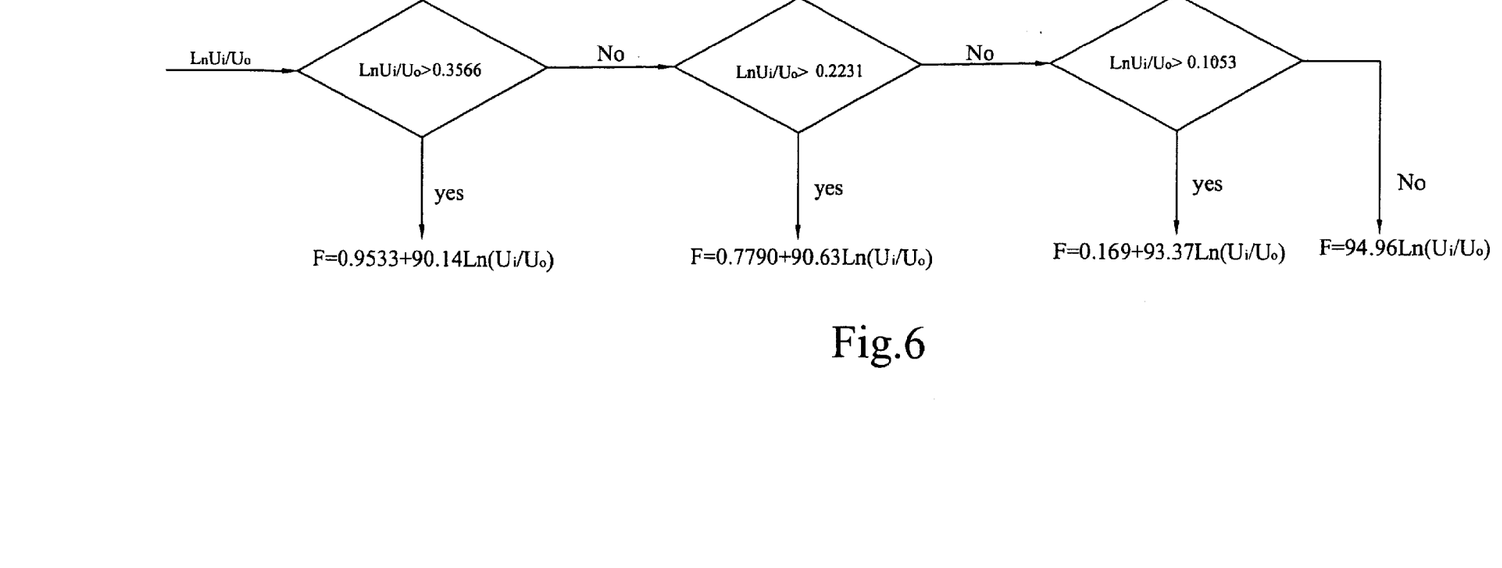
FIG. 6 is a diagram of flow prediction at broken line position in implementation.

High precision nucleon scale's calculation formula: $F=b_j+k_j Ln(U_i/U_0)$. Here $b_j$, $k_j$ separately represents above mentioned each line's cut off distance and sloping rate. The nucleon scale operates according to the diagram of flow prediction at broken line position as shown in FIG. 6.

2) Joint with multi-items formula: For multi-items formula $F=a_0+a_1(LnU_i/U_0)+a_2(LnU_i/U_0)^2+ \ldots +a_k(LnU_i/U_0)^k$ (k=0, 1, 2, . . . k) to assume coordinate points still are o, a, b, c, d to joint with 2 exponents 3 items formula. Use minimum 2 multiplication method to get $a_0$, $a_1$, $a_2$ as:
$a_0$=0.019324

$a_1$=95.3145
$a_2$=−6.62383

So $F=a_0+a_1(LnU_i/U_0)+a_2(LnU_i/U_0)^2$=0.019324 +95.3145×$(LnU_i/U_0)$+(−6.62383)×$(LnU_i/U_0)^2$

The nucleon scale operates according to this formula.

Comparing multi-items formula $F=a_0+a_1(LnU_i/U_0)+a_2(LnU_i/U_0)^2$ calculation result to existing nucleon scale used formula $F=KLn(U_i/U_0)$:

a) using multi-items formula to calculate a, b, c, d each point's load F, accumulative weight $W_h$ of mass material with error a as shown by data in right half of Table 3.

b) Using existing nucleon scale's formula to calculate a, b, c, d each point's load F, accumulative weight W of mass material with error as shown by date in left half of Table 3.

TABLE 3

| | Average value | Existing nucleon scale | | | | This invention's nucleon scale | | | |
|---|---|---|---|---|---|---|---|---|---|
| Measuring oint | Of Ln $(U_i/U_0)_{aAVG}$ | F (kg/m) | $W_h$ (kg) | $W_B$ (kg) | σ (%) | F (kg/m) | $W_h$ (kg) | $W_B$ (kg) | σ (%) |
| A | 0.10536 | 9.999 | 1799.8 | 1800 | −0.007 | 9.9824 | 1796.8 | 1800 | −0.23 |
| B | 0.22314 | 21.185 | 3177.8 | 3150 | +0.88 | 20.954 | 3143.6 | 3150 | −0.21 |
| C | 0.35667 | 33.862 | 4402.1 | 4303 | +2.3 | 33.166 | 4311.5 | 4303 | +0.16 |
| D | 0.51082 | 48.021 | 5335.6 | 5172 | +3.1 | 46.977 | 5167.5 | 5172 | −0.08 |

It's clear that accuracy of high precision nucleon scale to apply this method is raised comparatively higher than the existing nucleon scale.

Figure 7A:
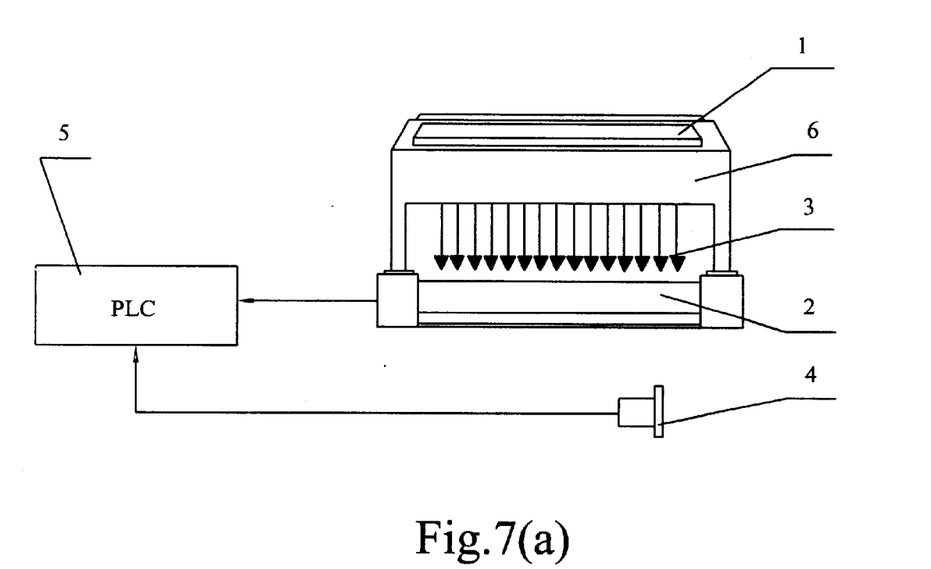
FIG. 7(a) is a diagram of this invention's nucleon scale (with line gamma radiation sources) in implementation.

FIG. 7(a) shows a concrete implementation scheme of this invention's nucleon scale with the line gamma radiation sources (close to parallel beamed gamma radiation) in spreading in one line.

Figure 7B:
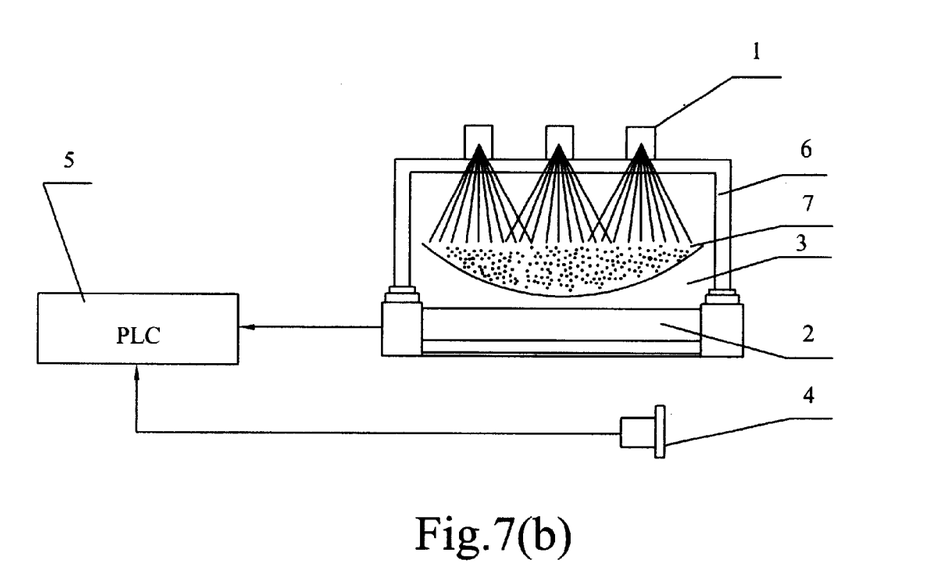
FIG. 7(b) is a diagram of this invention's nucleon scale (with multiple point gamma radiation sources) in implementation.

FIG. 7(b) shows a concrete implementation scheme of this invention's nucleon scale with 3 point gamma radiation sources spreading in one line.

According to the condition of mass material to be measured the gamma radiation source can be selected from one of 3 different radiation sources such as $^{137}$Cs (Cesium-137), $^6$Co (Cobalt-60) and $^{241}$Am (Americium-241).

Figures 8, 9:
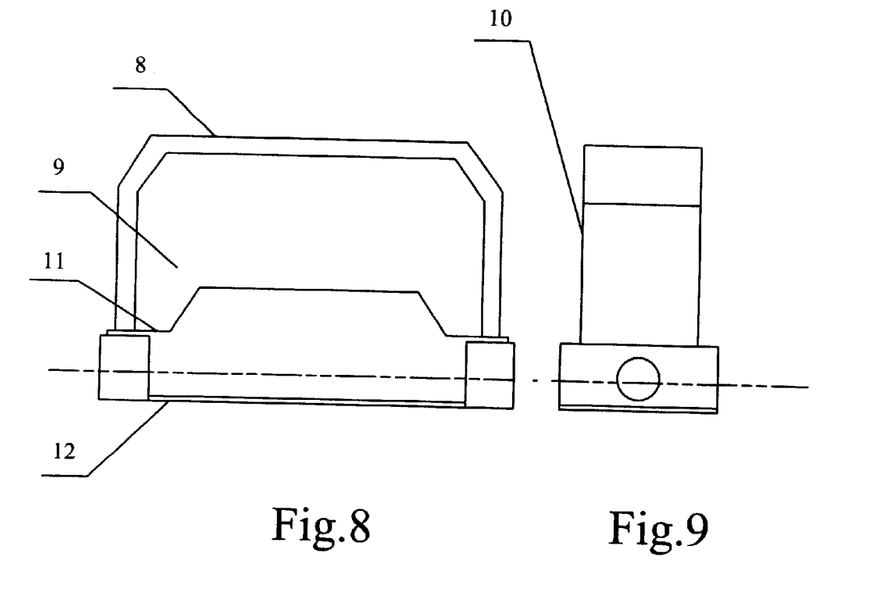
FIG. 8 is a diagram of the structure of completely enclosed scale frame.
FIG. 9, is a side view of FIG. 8.
Figure 10:
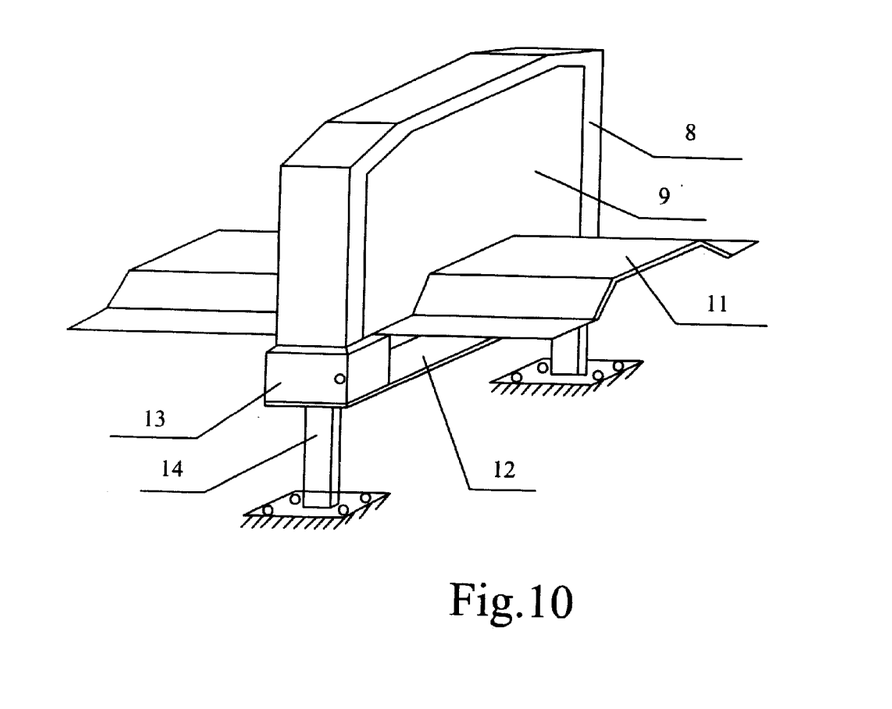
FIG. 10 is a three-dimensional view of a completely enclosed scale frame.

One form of this invention as shown in FIGS. 8 to 10 provides a nucleon scale with the structure of completely enclosed scale frame. This nucleon scale includes a main frame (8), a front panel (9), a back panel (10), a safe cover (11), a base plate (12), a end box (13), and a box foot (14). The completely enclosed scale frame plays very good shielding role to gamma radiation so it makes the high precision nucleon scale safe and reliable.

DPU in this invention can use industrial control machine such as PLC made in SIEMENS company.

Performance comparison of measuring method between this invention's high precision nucleon scale employing the method and existing nucleon scale is shown in Table 4.

$$W = \sum_{i=1}^{n} KLn(U_i/U_0)V_i$$

wherein the mass material's rated coefficient K is corrected by the DPU.

2. The method of claim 1 wherein said mass material's rated coefficient K is determined by the further steps of:
(i) weighing the mass material's steady load flow weight $W_{aB}$ with a scale and then inputting the value for $W_{aB}$ into the DPU;
(ii) inputting the measured output voltage $U_i$ instantaneously collected from gamma ray detector, the speed sensor's moving speed $V_i$ and a transmission time $t_i$ into the DBU and calculating a value $F_{Ba}$ using the formulae:

TABLE 4

| Nucleon sacle items | Existing nucleon scale | This invention's nucleon scale |
| --- | --- | --- |
| 1, Scale body | Single radiation source, fan beamed gamma radiation causing rather big influence to measuring precision from change of mass material's load, piling shape with difference of material positions | Multiple point radiation sources, or more close to parallel beamed gamma radiation therefore, it can reduce or eliminate influence to measuring precision from change of mass material's load, piling shape with difference of material positions |
| 2, Calculation formula | $F = KLn (U_i/U_0)$ | $F = b_j + k_j Ln (U_i/U_0)$ |
| 3, Coefficient K | K = Constant | K = f (F), variation parameter |
| 4, Flow range | Only suits for flow with rated K, within certain range | Suits for (0–100%) maximum flow range |
| 5, Precision | Measuring precision normally is 1–3% | Precision can be raised to 0.5% |
| 6, Safety | Scale frame open, radiation source exposed with lower safety | Completely enclosed scale frame, radiation source puts inside the frame with high safety |

I claim:

1. A method for the high precision measurement of a mass of material comprising the steps of:

installing multiple gamma radiation sources with corresponding gamma ray detectors and between them installing a material conveying device;

measuring the gamma ray detector's output voltage $U_0$ corresponding to situations when no mass of material is present and output voltage $U_i$ corresponding to situations when a mass of material is present and inputting the measured $U_0$ and $U_i$ values into a DPU connected to the gamma ray detector;

measuring the conveying devices moving speed $V_i$ using a high speed detector and inputting the measured value $V_i$ into the DPU;

calculating the accumulative mass material weight W conveyed in a period of time with the DPU using the formula:

$$F_{Ba} = \frac{W_B}{\sum_{i=1}^{n} V_i t_i} \quad \left(Ln\frac{u_i}{u_0}\right)_{aAVG} = \frac{\sum_{i=1}^{n} Ln\frac{U_i}{U_0}}{n}$$

(iii) establishing a coordinate system with $F_B$ as ordinate and $LnU_i/U_0$ as abscissa;
(iv) determining point a on the coordinate system as the intercept of the calculated $F_{Ba}$ and average value of $(LnU_i/U_0)_{aAVG}$ and to get $K_a$ the sloping rate of 0a; and
(v) repeating steps (i)–(iv) to determine points b, c, d . . . in the coordinate system which corresponding to different weights of mass material $W_{bB}$, $W_{cB}$, $W_{dB}$ . . . so as to get $K_b$, $K_c$, $K_d$ . . . and functional relation of $F_B=f(LnU_i/U_0)$.

3. The method of claim 2 wherein multi-section linear relation formula $F=bj+kLn(U_i/U_0)$ is used to replace function $F_B=f(LnU_i/U_0)$, where j is number of lines by the further steps of:
(1) connecting points 0a, ab, bc, cd, . . . to form a line; and
(2) using the coordinate value for points 0, a, b, c, d, . . . to obtain a value for each line's cut-off distance ($b_j$) and sloping rate ($k_j$).

4. The method of claim 2 wherein material load F is calculated using multi-items formula method to joint function $F_B=f(LnU_i/U_0)$ and for the coordinate value of points a, b, c, d, . . . in the coordinate system by using minimum 2 multiplication method wherein coefficients $a_1, a_2, a_3, \ldots a_k$ are derived from multi-items formula:

$$F=a_0+a_1(LnU_i/U_0)+a_2(LnU_i/U_0)^2+ \ldots +a_k(LnU_i/U_0)^k \text{ where } k=0, 1, 2, 3, \ldots k.$$

5. A nucleon scale comprising:

1–N gamma radiation sources where N=2–10;

a gamma ray detector corresponding to each gamma radiation sources wherein each gamma ray detector can transfer the received gamma ray intensity into voltage parameters;

a mass material conveying device located between each gamma radiation source and the corresponding receiver;

a speed sensor for measuring the speed of the conveying device; and a DPU connected to the gamma ray detectors and to the speed sensor wherein the DPU calculates the mass material's accurate weight according to the voltage parameters and the conveying device speed, wherein each gamma radiation source and corresponding gamma ray detectors are fixed in place by an enclosed scale frame.

6. The scale of claim 5 wherein said gamma ray sources can be selected from $^{137}$Cs, $^{60}$Co, $^{241}$Am in respect of mass material to be measured.

7. The scale of claim 5 wherein the number of gamma radiation sources is from 2 to 7.

* * * * *